United States Patent [19]

Mifune et al.

[11] 4,334,010
[45] Jun. 8, 1982

[54] SILVER HALIDE PHOTOGRAPHIC LIGHT-SENSITIVE ELEMENT

[75] Inventors: Hiroyuki Mifune; Shoji Ishiguro; Tadao Shishido; Yoshiharu Fuseya, all of Minami-ashigara; Teruaki Tsujikawa, Otsu, all of Japan

[73] Assignee: Fuji Photo Film Co., Ltd., Kanagawa, Japan

[21] Appl. No.: 284,164

[22] Filed: Jul. 17, 1981

[30] Foreign Application Priority Data

Jul. 17, 1980 [JP] Japan .................................. 55-97934

[51] Int. Cl.³ .............................................. G03C 1/34
[52] U.S. Cl. .................................. 430/551; 430/611; 430/613; 430/599; 430/600; 430/603; 430/607; 430/543; 430/570
[58] Field of Search ............... 430/611, 613, 599, 600, 430/603, 607, 551, 570, 543

[56] References Cited

U.S. PATENT DOCUMENTS 3,165,410  1/1965  Wilson ................................ 430/599
3,447,926  6/1969  Beckett et al. ...................... 430/551

Primary Examiner—Won H. Louie, Jr.
Attorney, Agent, or Firm—Sughrue, Mion, Zinn, Macpeak and Seas

[57] ABSTRACT

A silver halide photographic light-sensitive element is described comprising a support having thereon at least one silver halide emulsion layer, wherein at least one compound represented by formula (I) is incorporated in the silver halide emulsion layer or in another hydrophilic colloid layer:

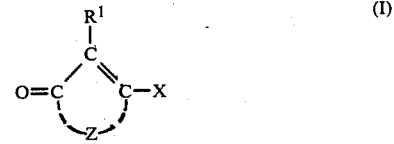

(I)

wherein X represents a hydroxy group or a group represented by

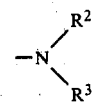

wherein $R^2$ and $R^3$ (which may be the same or different) each represents hydrogen, an alkyl group, or an aryl group; $R^1$ represents a sulfur-containing saturated heterocyclic group or a group represented by -A-S-B, wherein A represents an alkylene group and B represents hydrogen, an alkyl group, or an aryl group; and Z represents an atomic group forming a 5-membered or 6-membered unsubstituted or substituted carbocyclic ring.

In the silver halide photographic light-sensitive element, the so-called "latent image fading" phenomenon is prevented without accompanying degradation of other photograhic properties.

27 Claims, No Drawings

SILVER HALIDE PHOTOGRAPHIC LIGHT-SENSITIVE ELEMENT

FIELD OF THE INVENTION

The present invention relates to a silver halide photographic light-sensitive element, and more particularly to a silver halide photographic light-sensitive element in which latent image fading is prevented.

BACKGROUND OF THE INVENTION

As is known in the art, the formation of an image according to a silver halide photographic method requires a projection light-exposure process to form a latent image, and a development processing process to convert the latent image thus-formed into the corresponding silver or dye image. See, for example, Mees & James, *The Theory of the Photographic Process*, 4th ed., 1977.

The formation of a latent image according to projection light-exposure process results from extremely small changes in silver halide crystals when considered from a chemical standpoint, and the latent image itself is essentially unstable. Over a period from the time of the projection light-exposure process to the time of the development processing process, the intensity of the latent image is liable to decrease. This phenomenon is generally called "latent image fading". Usually the latent image fading results in disadvantageous reduction of the photographic sensitivity. The progress of the latent image fading varies generally depending on the conditions under which an exposed light-sensitive element is stored; for example, when the exposed light-sensitive element is stored at a high temperature, the latent image fading is generally significant, whereas when stored at a low temperature, it is generally less significant.

One simplified method for overcoming disadvantages resulting from the latent image fading is to carry out the development processing immediately after the projection light-exposure, and a second simplified method is to store the exposed light-sensitive element at a low temperature. Although these methods are the easiest from a chemical standpoint, they are often not convenient for the user. Negative elements and reversal elements are often allowed to stand at room temperature for several months after projection light-exposure before they are subjected to development processing. Even positive elements for duplication are sometimes allowed to stand for several months.

It is therefore desirable to prepare a silver halide photographic light-sensitive element which is capable of preventing the fading of latent image by application of a specific procedure in the course of the production thereof. In order to obtain such light-sensitive elements, various methods have heretofore been proposed.

SUMMARY OF THE INVENTION

Therefore, an object of the present invention is to provide a silver halide photographic light-sensitive element in which the fading of latent image during storage after the projection light-exposure is sufficiently prevented.

Another object of the present invention is to provide a siler halide photographic light-sensitive element containing a compound which is capable of preventing latent image fading without accompanying the degradation of other photographic properties.

A further object of the present invention is to provide a silver halide photographic light-sensitive element containing a compound which is capable of sufficiently preventing the latent image fading even when used in an extremely small amount.

As a result of extensive investigations in order to achieve the above-described objects, it has now been found that a compound in which the carbon atom at the 2-position of a 3-hydroxy-2-cyclohexen-1-one, a 3-amino-2-cyclohexen-1-one, a 3-hydroxy-2-cyclopenten-1-one or a 3-amino-2-cyclopenten-1-one is substituted with a sulfur-containing saturated heterocyclic group or a group represented by -A-S-B, wherein A represents an alkylene group and B represents hydrogen, an alkyl group, or an aryl group, can provide a very useful effect of preventing latent image fading.

The present invention, therefore, provides a silver halide photographic light-sensitive element comprising a support having thereon at least one silver halide emulsion layer, wherein at least one compound represented by formula (I) is incorporated in the silver halide emulsion layer or in another hydrophilic colloid layer:

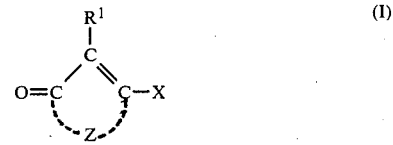
(I)

wherein X represents a hydroxy group or a group represented by

wherein $R^2$ and $R^3$ (which may be the same or different) each represents hydrogen, an alkyl group, or an aryl group; $R^1$ represents a sulfur-containing saturated heterocyclic group or a group represented by -A-S-B, wherein A represents an alkylene group and B represents hydrogen, an alkyl group, or an aryl group; and Z represents an atomic group forming a 5-membered or 6-membered unsubstituted or substituted carbocyclic ring.

DETAILED DESCRIPTION OF THE INVENTION

In formula (I), X represents a hydroxy group or a group represented by

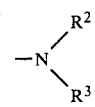

wherein $R^2$ and $R^3$ (which may be the same or different) each represents hydrogen, an alkyl group (preferably an alkyl group having from 1 to 5 carbon atoms, and specific examples being, for example, a methyl group, an ethyl group, etc.) or an aryl group (preferably a phenyl group). It is also preferred that one of $R^2$ and $R^3$ is hydrogen.

R[1] represents a sulfur-containing saturated heterocyclic group or a group represented by -A-S-B, wherein A represents an alkylene group and B represents hydrogen, an alkyl group, or an aryl group.

The sulfur-containing saturated heterocyclic group represented by R[1] is a saturated heterocyclic group containing at least one sulfur atom as one of the ring-constituting members, and preferably is a saturated heterocyclic group which has five or six ring constituting members including the sulfur atom and which is connected to the carbocyclic ring in formula (I) through a carbon atom adjacent to the sulfur atom. Specific examples of the sulfur-containing saturated heterocyclic group include a 2-tetrahydrothienyl group, and a tetrahydrothiopyranyl group. The heterocyclic group may be one or more substituents, such as a methyl group, an ethyl group, a methoxy group, an acetamido group, etc.

In the group represented by -A-S-B for R[1], examples of the alkylene group A are preferably lower alkylene group, especially a methylene group. The alkyl group for B is preferably an alkyl group having from 1 to 12 carbon atoms, for example, a methyl group, an ethyl group, etc. The aryl group for B is preferably a phenyl group. Specific examples of the group represented by -A-S-B include a mercaptoethyl group, an ethylthiomethyl group, a dodecylthiomethyl group, and a phenylthiomethyl group.

Of the groups for R[1], a sulfur-containing saturated heterocyclic group is preferred, and a 2-tetrahydrothienyl group and a 2-tetrahydrothiopyranyl group are particularly preferred.

Z represents an atomic group forming a 5-membered or 6-membered carbocyclic ring, that is, an atomic group forming a cyclopentene ring or a cyclohexene ring. The carbocyclic group may not have any substituent on the portion represented by Z, or may have one or more substituents on the portion represented by Z. Examples of the substituents include an alkyl group (preferably an alkyl group having from 1 to 5 carbon atoms, for example, a methyl group, an ethyl group, etc.), an aryl group (preferably a phenyl group which may be substituted, examples of the substituents being an alkyl group, for example, a methyl group, an ethyl group, an n-propyl group, an isopropyl group, etc., an alkoxy group, for example, a methoxy group, an ethoxy group, etc., a halogen atom, for example, a chlorine atom, a bromine atom, etc., and specific examples being a phenyl group, a p-tolyl group, a p-isopropylphenyl group, a p-methoxyphenyl group, a 3,4-dimethoxyphenyl group, a 3,4,5-trimethoxyphenyl group, and a 3,4-dichlorophenyl group.

The compound represented by formula (I) may have a tautomeric structure of a 1,3-dione form when X represents a hydroxy group or a tautomeric structure of a 1-imino-3-one form when X represents a group represented by

wherein at least one of R[2] and R[3] represents hydrogen. In these cases, a compound having either structure has an effect where latent image fading is prevented and thus these compounds are set forth using the 2-cyclohexen-1-one form or the 2-cyclopenten-1-one form in the specification.

Furthermore, the compound represented by formula (I) can be used in an appropriate salt form, and formula (I) as used herein include such salt form. The salt form compounds are used in the same manner as the non-salt form compound. Examples of useful salts include an inorganic acid salt such as a hydrochloride, a sulfate, etc., an organic acid salt such as an acetate, etc., or the like. In the compound represented by formula (I), where X represents a group represented by

wherein R[2] and R[3] each represents the same meaning as defined above, the compound tends to have the salt form while synthesizing, but where X represents a hydroxy group, the compound never have the salt form.

Specific examples of the compound represented by formula (I) according to the present invention are illustrated below, but the present invention is not to be construed as being limited to these compounds.

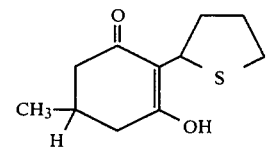

1.

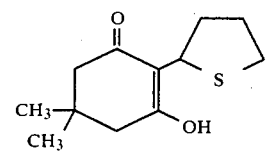

2.

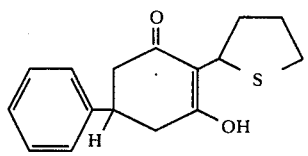

3.

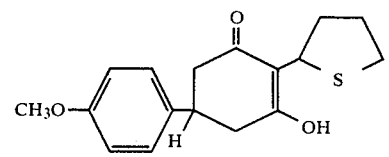

4.

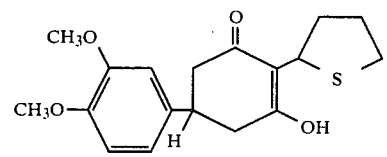

5.

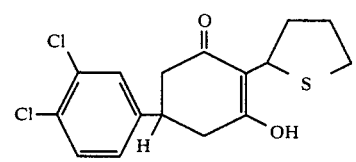

6.

-continued

7. 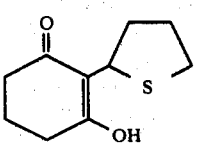

8. 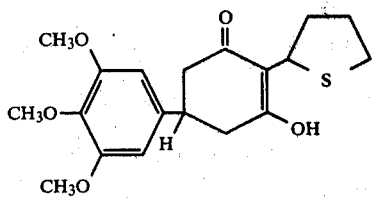

9. 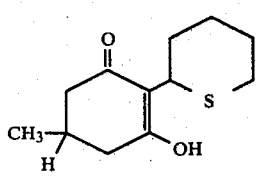

10. 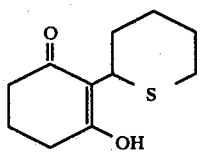

11. 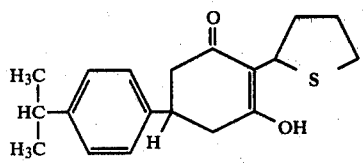

12. 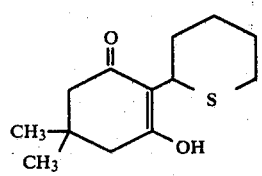

13. 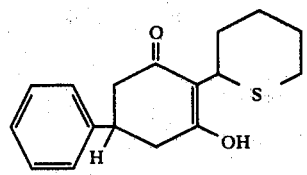

14. 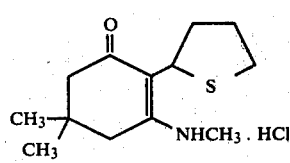

15. 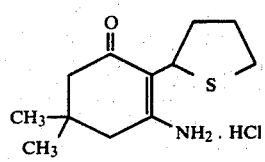

-continued

16. 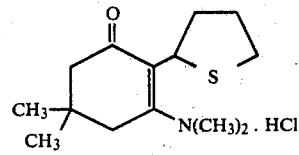

17. 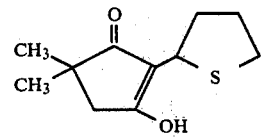

18. 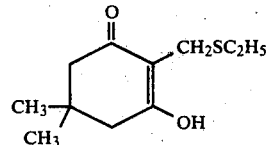

19. 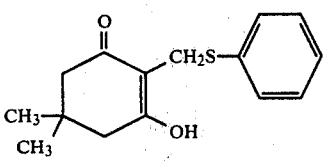

20. 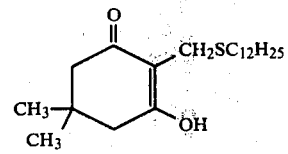

Compounds represented by formula (I) can be easily synthesized by the methods described, for example, in T. Tsujikawa and M. Hayashi, *Chem. Pharm. Bull.* (Tokyo), Vol. 25, pages 3147 to 3154 (1977), E. E. Smissman, J. R. J. Sorenson, W. A. Albrecht and M. W. Creese, *J. Org. Chem.*, Vol. 35, pages 1357 to 1360 (1970), Japanese Patent Application (OPI) No. 30151/79 and British Pat. No. 779,216.

Hereinafter, the methods of synthesizing the compounds will be explained with reference to representative examples. That is, the compound represented by the formula (I) wherein X is a hydroxy group and $R^1$ is a sulfur-containing saturated heterocyclic group, for example, 2-(2-tetrahydrothienyl)-3-hydroxy-5,5-dimethyl-2-cyclohexen-1-one, can be synthesized by heating dimedone and 2,3-dihydroxy thiophene in an appropriate solvent (for example, benzene, etc.) in the presence of an acid or by heating dimedone and 2-chlorotetrahydrothiophene in an appropriate solvent (for example, benzene, etc.). The compound represented by formula (I) wherein X is a group represented by

and $R^1$ is a sulfur-containing saturated heterocyclic group, for example, 3-amino-2-(2-tetrahydrothienyl)-5,5-dimethyl-2-cyclohexen-1-one can be synthesized by a method in which 2-(2-tetrahydrothienyl)-3-hydroxy-5,5-dimethyl-2-cyclohexen-1-one is chlorinated with oxalic chloride in a conventional manner to obtain the 3-chloro compound, and then the latter is reacted with ammonia or a method in which 2-(2-tetrahydrothienyl)-3-hydroxy-5,5-dimethylcyclohexen-1-one is reacted with diazomethane to obtain the 3-methoxy compound, and then the latter is reacted with ammonia. The compound represented by formula (I) wherein X is a hydroxy group and $R^1$ is a group represented by -A-S-B, for example, 3-hydroxy-5,5-dimethyl-2-phenylthiomethyl-2-cyclohexen-1-one can be synthesized by heating N-phenylthiomethylpiperidine hydrochloride and dimedone in an appropriate solvent (for example, dioxane, etc.), and 2-ethylthiomethyl-3-hydroxy-5,5-dimethyl-2-cyclohexen-1-one can be synthesized by reacting dimedone, formalin and ethyl-mercaptan in an appropriate solvent (for example, methanol, etc.) in the presence of sodium hydroxide.

The compound represented by formula (I) can be incorporated into any one or more of the hydrophilic colloid layers of a silver halide photographic light-sensitive element. It may be incorporated into either a silver halide emulsion layer or a light-insensitive layer, or example, a protective layer, an intermediate layer, a filter layer, or the like, by known procedures. For example, when the compound is water-soluble, it is added as an aqueous solution having a suitable concentration, and when insoluble or sparingly soluble in water, it is dissolved in an organic solvent which is selected from water-miscible ones, such as alcohols, ethers, glycols, ketones, esters, and amides, which exerts no adverse effect on photographic characteristics, and added as a solution to an emulsion or a hydrophilic colloid. For this purpose, those well known methods which are used to add a water-insoluble coupler to an emulsion in the form of a dispersion can be employed.

The time of the addition of the compound according to the present invention is not particularly restricted, and the compound may be added at any desired time between after physical ripening and immediately before coating.

The compound represented by formula (I) exhibits the effect of preventing latent image fading in an extremely small amount of less than 0.1 g per mole of silver. When the compound is added in an amount of 0.1 g/mol Ag or more, the problem that the fog rather increases may occur, and thus the compound is usually used in an amount of less than 0.1 g/mol Ag. The compound represented by formula (I) is preferably used within the range of from 0.05 mg/mol Ag to 100 mg/mol Ag, and particularly preferably within the range of from 0.1 mg/mol Ag to 50 mg/mol Ag.

Silver halide in a silver halide light-sensitive element as used in this invention comprises silver chloride, silver chlorobromide, silver bromide, silver iodobromide or silver iodochlorobromide. While the average particle size of silver halide particles is not critical, it is preferably not greater than $3\mu$.

The silver halide emulsion is usually subjected to chemical sensitization although a so-called primitive emulsion, which is not subjected to chemical sensitization, can be used. For this chemical sensitization, those methods as described in the literatures by Glafkides and Zelikman et al., and H. Frieser edit., *Die Grundlagen der Photographischen Prozesse mit Silberhalogeniden* (Akademische Verlagsgesellschaft, 1968) can be used. That is, a sulfur sensitization method in which thiosulfates, thioureas, thiazoles, rhodanines, etc., or active gelatin is used, a reduction sensitization method in which stannous salts, amines, hydrazines, formamidinesulfinic acid, silane compounds or the like are used, a noble metal sensitization method in which gold complex salts and complex salts of metals belonging to Group VIII of the Periodic Table, such as platinum, iridium, and palladium, are used, and so forth can be used singly or in combination with each other.

Furthermore, the compound according to the present invention can be used in combination with the above-described known chemical sensitizers, in chemical ripening.

For the purposes of increasing sensitivity and contrast, and of accelerating development, for example, polyalkylene oxide or its derivatives, such as ethers, esters, and amines, thioether compounds, thiomorpholines, quaternary ammonium salt compounds, urethane derivatives, urea derivatives, imidazole derivatives, and 3-pyrazolidones may be incorporated. For example, such compounds as described in U.S. Pat. Nos. 2,400,532, 2,423,549, 2,716,062, 3,617,280, 3,772,021, 3,808,003, etc., can be used.

For the purpose of preventing fog from occuring in the course of production, storage, or photographic processing of a light-sensitive element, or of stabilizing photographic characteristics, various compounds can be incorporated. For example, the following compounds known as anti-foggants or stabilizers can be used: azoles, such as benzothiazolium salts, nitroindazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, and mercaptotetrazoles (particularly, 1-phenyl-5-mercaptotetrazole); mercaptopyrimidines; mercaptotriazines; thioketo compounds, such as oxazolinethione; azaindenes, such as triazaindenes, tetrazaindenes (particularly, 4-hydroxy-substituted(1,3-,3a,7)tetrazaindenes), and pentazaindenes; and benzenesulfinic acid, benzenesulfonic acid amide.

In this invention, it is advantageous to use gelatin as a binder for the photographic emulsion and as a protective colloid, but other hydrophilic colloids can be used. Hydrophilic colloids which can be used include proteins, such as gelatin derivatives, graft polymers of gelatin and other polymers, albumin, and casein; cellulose derivatives, such as hydroxyethyl cellulose, carboxymethyl cellulose, and cellulose sulfuric acid ester; sugar derivatives, such as sodium alginate, and starch derivatives; and a wide variety of synthetic hydrophilic homo- or copolymeric substances, such as polyvinyl alcohol, a partial acetal of polyvinyl alcohol, poly-N-vinyl pyrrolidone, polyacrylic acid, polymethacrylic acid, polyacrylamide, polyvinyl imidazole, and polyvinyl pyrazole.

Gelatin as used herein may be either lime-processed gelatin or acid-processed gelatin. Additionally, a gelatin hydrolytic product and a gelatin enzyme-decomposition product can be used instead of gelatin.

The photographic emulsion layer and other hydrophilic colloid layers of the light-sensitive element of this invention may contain various known surface active agents as auxiliary coating agents or for the purposes of preventing electrification, improving sliding properties, emulsification-dispersion, preventing adhesion, and photographic characteristics (for example, acceleration of development, an increase in contrast, and sensitization), and so forth.

Surface active agents which can be used include: nonionic surface active agents, such as saponin, alkylene oxide derivatives (e.g., polyethylene glycols, polyalkylene glycol alkyl amines or amides, and polyethylene oxide adducts of silicone), glycidol derivatives (e.g., alkenyl succinic acid polyglyceride), aliphatic acid esters of polyhydric alcohols, alkyl esters of sugar, urethanes of sugar, and ethers of sugar; anion surface active agents, such as triterpenoid-based saponin, alkylcarboxylic acid salts, alkylbenzenesulfonic acid salts, alkylsulfuric acid esters, alkylphosphoric acid esters, N-acyl-N-alkyltaurines, sulfosuccinic acid esters, and sulfoalkylpolyoxyethylene alkylphenyl ethers; amphoteric surface active agents, such as amino acids, aminoalkylsulfonic acids, aminoalkylsulfonic acid or aminoalkylphosphoric acid esters, alkylbetaines, amineimides, and amineoxides; and cation surface active agents, such as alkylamine salts, aliphatic or aromatic quaternary ammonium salts, heterocyclic quaternary ammonium salts, such as pyridinium, and imidazolium, and aliphatic or heterocyclic ring-containing phosphonium or sulfonium salts.

In the photographic light-sensitive element of this invention, the photographic emulsion layer and other hydrophilic colloid layers may contain therein a dispersion of a water-insoluble or water-sparingly soluble synthetic polymer for the purposes of improving dimension stability and so forth. Synthetic polymers which can be used include homo- or copolymers of alkyl acrylate or methacrylate, alkoxyalkyl acrylate or methacrylate, glycidyl acrylate or methacrylate, acrylamide or methacrylamide, vinyl ester (e.g., vinyl acetate), acrylonitrile, olefin, and styrene, and copolymers of the above monomers and acrylic acid, methacrylic acid, $\alpha,\beta$-unsaturated dicarboxylic acid, hydroxylalkyl acrylate or methacrylate, sulfoalkyl acrylate or methacrylate, styrenesulfonic acid, etc.

Furthermore, the photographic emulsion layer and other hydrophilic colloid layers of the photographic light-sensitive element of the present invention may contain therein an inorganic or organic hardener. As such hardeners, chromium salts (e.g., chromium alum and chromium acetate), aldehydes (e.g., formaldehyde, glyoxal, glutaraldehyde), N-ethylol compounds (e.g., dimethylol urea and methyloldimethylhydantoin), dioxane derivatives (e.g., 2,3-dihydroxydioxane), active vinyl compounds (e.g., 1,3,5-triacryloyl-hexahydro-S-triazine and bis(vinylsulfonyl) methyl ether), active halogen compounds (e.g., 2,4-dichloro-6-hydroxy-S-triazine), mucohalogenic acids (e.g., mucochloric acid and mucophenoxychloric acid), isooxazoles, dialdehyde starch, 2-chloro-6-hydroxy-triazinylated gelatin, and the like can be used, singly or in combination with each other.

The photographic emulsion of this invention may be spectrally sensitized by use of methine dyes and the like. Dyes which can be used include cyanine dye, merocyanine dye, complex cyanine dye, complex merocyanine dye, holopolar cyanine dye, hemicyanine dye, styryl dye and hemioxonol dye. Particularly useful dyes are merocyanine dyes and complex merocyanine dyes. These dyes can include any nuclei which are known to be utilized in cyanine dyes as basic heterocyclic nuclei.

Basic heterocyclic nuclei which can be used include a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc.; nuclei in which an alicyclic hydrocarbon ring is condensed together with the above-described nuclei; and nuclei in which an aromatic hydrocarbon ring is condensed together with the above-described nuclei, such as an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, and a quinoline nucleus. The nucleus of the basic heterocyclic nucleus may contain substituents on the carbon atoms present in the basic heterocyclic nucleus.

The merocyanine dye or complex merocyanine dye can include, as a nucleus having the ketomethylene structure, a 5- or 6-membered heterocyclic nucleus, such as a pyrazoline-5-one nucleus, a thiohydantoin nucleus, a 2-thioxazolidine-2,4-dione nucleus, a thiazolidine-2,4-dione nucleus, a rhodanine nucleus, and a thiobarbituric acid nucleus.

In the light-sensitive element of this invention, he hydrophilic colloid layer may contain therein a water-soluble dye (e.g., oxonol dye, hemioxonol dye, styryl dye, merocyanine dye, cyanine dye, and azo dye) as a filter dye or for the purposes of prevention of irradiation and so forth.

The photographic emulsion of this invention may contain therein a color image-forming coupler (referred to as a coupler hereinafter), i.e., a compound which forms a dye upon reacting with an oxidation product of an aromatic amine (usually, a primary amine) developing agent.

In one preferred embodiment, the coupler has a hydrophobic group, referred to as a ballast group, in the molecule thereof, and is non-diffusible. The coupler may be either a 4-equivalent coupler or a 2-equivalent coupler. Furthermore, the photographic emulsion of this invention may contain therein a colored coupler having the color correction effect, or a coupler (referred to as a DIR coupler) releasing a development inhibitor as the development proceeds. The coupler may be a coupler which provides a colorless coupling reaction product.

As yellow color-forming couplers, known open chain ketomethylene based couplers can be used. Among these couplers, benzoylacetoanilide- and pivaloylacetoanilide-based compounds are advantageously used.

Magenta couplers which can be used include pyrazolone based compounds, indazolone based compounds, and cyanoacetyl compounds. Particularly advantageous among these compounds are pyrazolone based compounds.

Cyan couplers which can be used include phenol based compounds and naphthol based compounds.

DIR (development inhibitor releasing) couplers which can be used include those described, for example, in U.S. Pat. Nos. 3,227,554, 3,617,291, 3,701,783, 3,790,384, and 3,632,345, West German Patent Application (OLS) Nos. 2,414,006, 2,454,301, and 2,454,329, British Pat. No. 953,454, and Japanese Patent Application (OPI) No. 69624/77.

In addition to the DIR coupler, a compound which releases a development inhibitor as the development proceeds may be incorporated into the light-sensitive element of this invention. Examples of such compounds are described, for example, in U.S. Pat. Nos. 3,297,445 and 3,379,529, and West German Patent Application (OLS) No. 2,417,914.

Two or more of the above-described couplers can be incorporated into the same layer. The same coupler may be incorporated into two or more different layers.

The light-sensitive element of this invention may contain, as a color fog-preventing agent, a hydroquinone derivative, an aminophenol derivative, a gallic acid derivative, an ascorbic acid derivative, or the like.

Furthermore, the light-sensitive element of this invention may contain in its hydrophilic colloid layer an ultraviolet ray-absorbing agent, such as a benzotriazole compound which is substituted by an aryl group, a 4-thiazolidone compound, a benzophenone compund, a cinnamic acid ester compound, or a benzoxazole compound.

The photographic emulsion of this invention is coated on a flexible support, such as a plastic film (e.g., cellulose nitrate, cellulose acetate, and polyethylene terephthalate) and paper, or on a rigid support, which are usually used in production of photographic light-sensitive elements.

A multilayer, multicolor photographic element having at least two different sensitivities is included within the scope of this invention. Typically, the multilayer, multicolor photographic element comprises a support and at least one layer of each of a red-sensitive emulsion layer, of a green-sensitive emulsion layer, and of a blue-sensitive emulsion layer, provided on the support. The order in which the emulsion layers are provided on the support is not critical to this invention, and they can be arranged as desired based on other conventional considerations. Typically, the layers are coated on the support in the order: red-sensitive emulsion layer, green-sensitive emulsion layer, and blue-sensitive emulsion layer, containing therein a cyan-forming coupler, a magenta-forming coupler, and a yellow-forming coupler, respectively. For particular use, different combinations can be employed.

Light-exposure to obtain a photographic image in this invention can be performed by known methods. For this light-exposure, various known light sources, such as natural light (sunlight), a tungsten lamp, a fluorescent lamp, a mercury lamp, a xenon arc lamp, a carbon arc lamp, a xenon flash lamp, and a cathode flying spot, can be employed. Light-exposure time may be, of course, within the range of from 1/1,000 second to 1 second which is typical for a camera. Furthermore, light-exposure times of shorter than 1/1,000 second, for example, about $1/10^4$ to $1/10^6$ second when a xenon flash lamp or a cathode ray tube is used, and of longer than 1 second, can be used.

The light-sensitive element of this invention can be processed by conventional methods using known processing solutions. The processing temperature is usually selected within the range of from about 18° C. to about 50° C. However, temperatures lower than 18° C. and temperatures higher than 50° C. can be employed. According to the particular purpose, either a development processing for forming silver image (black-and-white photographic processing) or a color photographic processing comprising a development processing for forming dye images can be used.

A developer for use in black-and-white photographic processing can contain therein a known developing agent. Developing agents which can be used include dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds as described in U.S. Pat. No. 4,067,872 wherein a 1,2,3,4-tetrahydroquinoline ring and an indolene ring are condensed together. These developing agents can be used alone or in combination with each other.

Generally, the developer may further contain therein known preservatives, alkali agents, pH buffers, antifoggants, etc., and, if desired, auxiliary dissolving agents, color-controlling agents, development accelerators, surface active agents, defoaming agents, hard water-softening agents, hardeners, tackifiers, etc.

As fixers, known fixer compositions can be used. Fixing agents which can be used include thiosulfuric acid salts and thiocyanic acid salts. Additionally, organic sulfur compounds which are known to have the effect as a fixing agent can be used. The fixer may contain therein a water-soluble aluminum salt as a hardener.

A dye image can be formed by conventional methods. For example, a negative-positive process (as described, for example, in Journal of the Society of Motion Picture and Television Engineers, Vol. 61, pages 667 to 701 (1953)), a color reversal process in which a negative silver image is formed by developing with a developer containing therein a black-and-white developing agent, then subjected to at least one uniform light-exposure or to another suitable fog-producing processing, and subsequently is color-developed to obtain a positive dye image, and a silver dye bleaching process in which a photographic emulsion layer containing therein a dye is exposed to light and then developed to form a silver image, and the dye is bleached by the use of the silver image as a bleaching catalyst, can be used.

A color developer generally comprises an alkaline aqueous solution containing therein a color developing agent. Color developing agents which can be used include known primary aromatic amine developers, such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-methanesulfonamidoethylaniline, and 3-methyl-4-amino-N-ethyl-N-β-methoxyethylaniline).

Additionally, color developing agents as described in L. F. A. Mason, Photographic Processing Chemistry, Focal Press, pages 226 to 229 (1966), U.S. Pat. Nos. 2,193,015 and 2,592,364, Japanese Patent Application (OPI) No. 64933/73, etc., can be used.

The color developer can contain therein pH buffers, such as sulfurous acid salts of alkali metal, carbonic acid salts of alkali metal, boric acid salts of alkali metal, and phosphoric acid salts of alkali metal, development inhibitors or anti-foggants, such as bromide, iodide, organic anti-foggants, etc. Furthermore, if desired, a hard water-softening agent, a preservative, such as hydroxyamine, an organic solvent, such as benzyl alcohol and diethylene glycol, a development accelerator, such as polyethylene glycol, a quaternary ammonium salt, and an amine, a dye-forming coupler, a competition coupler, a fogging agent, such as sodium borohydride, an auxiliary developing agent, such as 1-phenyl-3-pyrazolidone, a tackifier, a polycarboxylic acid-based chelating agent as described in U.S. Pat. No. 4,083,723, an antioxidant as described in West German Patent Application (OLS) No. 2,622,950, etc., can be incorporated thereinto.

After the color development, the photographic emulsion layer is usually subjected to a bleach processing. The bleach processing may be performed simultaneously with a fixation processing, or separately therefrom.

Bleaching agents which can be used include multivalent metal (e.g., iron (III), cobalt (III), chromium (VI), and copper (II)) compounds, peracids, quinones, and nitroso compounds. For example, ferricyanides, dichromic acid salts, organic complex salts of iron (III) or cobalt (III), and complex salts of aminopolycarboxylic acids, such as ethylenediaminetetraacetic acid, nitrilotriacetic acid, and 1,3-diamino-2-propanoltetraacetic acid, and organic acids, such as citric acid, tartaric acid, and malic acid; persulfuric acid salts, and permanganic acid salts; nitrosophenol; etc., can be used.

Of these compounds, potassium ferricyanide, iron (III) sodium ethylenediaminetetraacetate and iron (III) ammonium ethylenediaminetetraacetate are particularly useful. Ethylenediaminetetraacetic acid iron (III) complex salts are useful either in an independent bleaching solution or in a combined bleach-fixing solution.

To the bleach or bleach-fixing solution there can be added bleach accelerators as described in U.S. Pat. Nos. 3,042,520 and 3,241,966, Japanese Patent Publication Nos. 8506/70 and 8836/70, etc., thiol compounds as described in Japanese Patent Application (OPI) No. 65732/78, and other various additives.

The photographic light-sensitive element of the present invention shows substantial prevention of latent image fading without degrading other photographic properties.

The photographic light-sensitive elements of this invention, therefore, are suitable for use, in particular, as projection light-sensitive elements (e.g., a black-and-white negative film, a color negative film, and a reversal film). Of course, they can also be used in other applications (e.g., a black-and-white or color printing paper).

Synthesis examples of the compounds represented by formula (I) according to the present invention are illustrated below. Parts are parts by weight.

SYNTHESIS EXAMPLE 1

Synthesis of Compound 3

A mixture of 4.0 parts of 5-phenyl-1,3-cyclohexanedione and 120 parts by volume of a 5% benzene solution of 2-chlorotetrahydrothiphene was refluxed by heating while stirring. After cooling to room temperature, the reaction mixture was washed with 40 parts by volume of water and then treated three times with 30 parts by volume of a 5% aqueous solution of sodium hydroxide. The aqueous layer was collected and washed with 30 parts by volume of ether. While maintaining the temperature of the solution below 10° C., the pH of the solution was controlled between 4 and 5 with the addition of 6 N hydrochloric acid. The light orange colored crystals thus deposited were collected and purified by passing through a column containing a silica gel using a solvent mixture of chloroform and benzene (5:1) as a spreading agent to obtain 2-(2-tetrahydrothienyl)-3-hydroxy-5-phenyl-2-cyclohexen-1-one in a form of colorless fine crystals. The melting point was 141° to 142° C. The yield was 2.4 parts.

In a manner analogous to the above compound 1 and Compound 12 were obtained by selection of appropriate starting materials.

Compound 1: 2-(2-tetrahydrothienyl)-3-hydroxy-5-methyl-2-cyclohexen-1-one, colorless prism like crystals having a melting point of 111° to 113° C., the starting material of which is 5-methyl-1,3-cyclohexanedione.

Compound 12: 2-(2-tetrahydrothiopyranyl)-3-hydroxy-5,5-dimethyl-2-cyclohexen-1-one, colorless prism-like crystals having a melting point of 158°0 to 160° C., the starting material of which is 5,5-dimethyl-1,3-cyclohexanedione.

SYNTHESIS EXAMPLE 2

Synthesis of Compound 2

A mixture of 7 parts of dimedone, 7 parts of 2,3-dihydrothiophene, 150 parts by volume of benzene and 0.7 parts of p-toluenesulfonic acid was refluxed by heating while stirring for 1 hour and 30 minutes and then allowed to stand at room temperature for 12 hours. The reaction mixture was washed with 50 parts by volume of water and then treated three times with 50 parts by volume of a 10% aqueous solution of sodium hydroxide. The aqueous layer was collected and the pH was adjusted to 2.0 with the addition of 6 N hydrochloric acid while maintaining the temperature thereof below 10° C. The light yellow colored crystals thus deposited were collected and purified by passing through a column containing a silica gel using a solvent mixture of chloroform and benzene (1:1) as a spreading agent to obtain 2-(2-tetrahydrothienyl)-3-hydroxy-5,5-dimethyl-2-cyclohexen-1-one in a form of colorless fine crystals. The melting point was 97° to 99° C. The yield was 8 parts.

SYNTHESIS EXAMPLE 3

Synthesis of Compound 15

To 500 parts by volume of an ether solution of diazomethane prepared using 47 parts of N-nitroso urea and 140 parts by volume of a 40% aqueous solution of potassium hydroxide in a conventional manner, 17.7 parts of 2-(2-tetrahydrothienyl)-3-hydroxy-5,5-dimethyl-2-cyclohexen-1-one was added little by little over a period of 20 minutes. After stirring for 15 hours at room temperature, the unreacted diazomethane was decomposed by the addition of 5 parts of acetic acid and washed with 1 N aqueous sodium hydroxide solution and then with a saturated aqueous sodium chloride solution followed by drying. After removing ether by distillation, the residue was passed through a column containing a silica gel using a solvent mixture of chloroform and benzene (1:3) as a spreading agent. Upon recrystallization of the raw product from a solvent mixture of benzene and n-hexane, 2-(2-tetrahydrothienyl)-3-methoxy-5,5-dimethyl-2-cyclohexen-1-one was obtained in the form of colorless scale-like crystals. The melting point was 111° to 112° C. The yield was 5.7 parts.

1.7 parts of the compound thus obtained and 40 parts of a 15% methanolic ammonia were heated at 80° C. in a sealed vessel for 6 hours. After condensation, the residue was dissolved in 50 parts by volume of benzene and the solution was twice treated with 20 parts by volume of 6 N hydrochloric acid. The aqueous layer was collected, washed with ether, the pH controlled between 8 to 9 with potassium carbonate, and extracted three times with 20 parts by volume of chloroform. Chloroform was distilled off and the residue was treated with 1.5 parts of a 30% ethanolic hydrochloric acid. After removing ethanol by distillation, the residue was recrystallized from a solvent mixture of ethanol and acetonitrile to obtain 3-amino-2-(2-tetrahydrothienyl)-5,5-dimethyl-2-cyclohexen-1-one hydrochloride. The melting point was 175° to 178° C. (decomposed). The yield was 1.0 part.

SYNTHESIS EXAMPLE 4

Synthesis of Compound 15 (different method)

3 parts of 2-(2-tetrahydrothienyl)-3-hydroxy-5,5-dimethyl-2-cyclohexen-1-one was added to 9.9 parts of oxalic chloride, the mixture was stirred at room temperature for 1.5 hours and concentrated at a temperature below 50° C. The residue was dissolved in 40 parts by volume of benzene and 1.0 part of pyrolidine was added thereto. After stirring at room temperature for 1 hour, the mixture was washed with water, a saturated aqueous sodium hydrogen carbonate solution, and a saturated aqueous sodium chloride solution, in the order listed, and then dried. Benzene was distilled off and the residue was passed through a column containing silica gel using a solvent mixture of chloroform and benzene (2:1) as a spreading agent to obtain 1.1 parts of 3-chloro-2-(2-tetrahydrothienyl)-5,5-dimethyl-2-cyclohexen-1-one as a brown colored oily product.

0.8 parts of the compound thus obtained and 13 parts of a 15% methanolic ammonia were heated at 100° C. in a sealed vessel for 10 hours. Methanol was distilled off and the residue was treated by the addition of 10 parts by volume of a 10% aqueous potassium carbonate solution and 10 parts by volume of chloroform. The organic layer was collected and chloroform was distilled off. The residue was passed through a column containing silic gel using chloroform as a spreading agent. Chloroform was distilled off, the residue was treated with an excess amount of 30% ethanolic hydrochloric acid and recrystallized from a solvent mixture of ethanol and acetonitrile to obtain 3-amino-2-(2-tetrahydrothienyl)-5,5-dimethyl-2-cyclohexen-1-one hydrochloride in the form of colorless fine crystals. The melting point was 174° to 175° C. (decomposed). Yield was 0.35 parts. When the compound thus obtained was mixed with the compound obtained in Synthesis Example 3 and melted, the depression of the melting point was not observed. The IR absorption spectra and NMR spectra of these compounds were consistent with each other.

SYNTHESIS EXAMPLE 5

Synthesis of Compound 18

36 parts by volume of 30% formalin, 42 parts of dimedone dissolved in 100 parts by volume of methanol and 29.5 parts by volume of 10 N aqueous sodium hydroxide solution were added to 17.5 parts of ethyl mercaptane and the mixture was allowed to stand for 2 days at room temperature. 295 parts by volume of N hydrochloric acid and 100 parts by volume of methanol were added to adjust the pH of the mixture was 4. The crystals deposited were collected and recrystallized from methanol to obtain 2-ethylthiomethyl-3-hydroxy-5,5-dimethyl-2-cyclohexen-1-one. The melting point was 134° C.

The present invention will be further explained in greater detail with reference to the following examples, but the present invention is not to construed as being limited to these examples.

EXAMPLE 1

To a silver iodobromide gelatin emulsion containing 6 mol% of silver iodide were added potassium chloroaurate in an amount of 2.8 mg per mol silver halide and potassium thiocyanate in an amount of 150 mg per mol silver halide, then sodium thiosulfate in an amount of 9.5 mg per mol silver halide, and further the compound shown in Table 1 were added, and the resulting mixture was subjected to ripening by heating at 60° C. for 60 minutes (average particle size of silver halide being about 0.8 microns).

To each emulsion was added 4-hydroxy-6-methyl-1,3,3a,7-tetraazaindene as a stabilizer, sodium dodecylbenzenesulfonate as a coating aid, and 2,4-dichloro-6-hydroxy-s-triazine as an hardening agent, and the resulting mixture was coated on a triacetyl cellulose film and dried to a thickness of 5 microns to obtain Samples 1 to 5.

These samples were exposed to light through an optical wedge for 1/20 second using a sensitometer, developed at 20° C. for 7 minutes with Kodak D-76 developer solution and then were fixed and washed with water in a conventional manner.

The photographic properties when the light-sensitive element sample was developed just after the light-exposure, and the photographic properties when such an element was developed after being allowed to stand under conditions of the temperature of 50° C. and the relative humidity of 75% for one week after the light-exposure are comparatively shown in Table 1. In Table 1, the photographic sensitivity is shown by a reciprocal value of a logarithm of a light-exposure amount required to obtain an optical density of fog value +0.2 and the sensitivity of Sample 1 when developed just after the light exposure is taken as 100 and the other sensitivities are shown relatively.

By comparing the results obtained in Samples 2 to 5 containing the compounds according to the present invention with the results obtained in the control sample, the extent of the sensitization and the latent image fading can be seen.

It is apparent from the results shown in Table 1 that the compounds according to the present invention are excellent in preventing the fading of latent image, even by the addition of an extremely small amount thereof, and exhibit some increase in the sensitivity in certain cases.

TABLE 1

| Sample No. | Compound | Amount Added (mg/mol AgX) | Developed Just after Light-exposure | | Developed after Standing at 50° C. and 75% RH for 1 Week after Light-exposure | |
|---|---|---|---|---|---|---|
| | | | Relative Sensitivity | Fog | Relative Sensitivity | Fog |
| 1 | None (control) | — | 100 | 0.06 | 71 | 0.08 |
| 2 | Compound-1 | 1.9 | 100 | 0.06 | 95 | 0.08 |
| 3 | Compound-1 | 5.7 | 100 | 0.06 | 100 | 0.08 |
| 4 | Compound-2 | 2.0 | 100 | 0.06 | 97 | 0.08 |
| 5 | Compound-2 | 6.2 | 105 | 0.06 | 106 | 0.08 |

EXAMPLE 2

Using the same silver halide gelatin emulsion as that used in Sample 1 of Example 1, and each of the compounds shown in Table 2 being added thereto just before coating on a triacetyl cellulose film Samples 11 to 27 were obtained. These samples were subjected to the same procedures as in Example 1 to obtain the results shown in Table 2.

TABLE 2

| Sample No. | Compound | Amount Added (mg/mol AgX) | Developed Just after Light-exposure | | Developed after Standing at 50° C. and 75% RH for 1 Week after Light-exposure | |
|---|---|---|---|---|---|---|
| | | | Relative Sensitivity | Fog | Relative Sensitivity | Fog |
| 11 | Control | — | 100 | 0.06 | 71 | 0.08 |
| 12 | Dimedone (Comparison) | 8 | 100 | 0.06 | 71 | 0.08 |
| 13 | Dimedone (Comparison) | 120 | 98 | 0.08 | 80 | 0.15 |
| 14 | Dimedone (Comparison) | 485 | 95 | 0.09 | 93 | 0.20 |
| 15 | Dimedone (Comparison) | 1474 | 90 | 0.12 | 92 | 0.25 |
| 16 | Compound 1 | 0.5 | 100 | 0.06 | 95 | 0.08 |
| 17 | Compound 1 | 4.9 | 100 | 0.06 | 100 | 0.08 |
| 18 | Compound 1 | 49.0 | 108 | 0.25 | 118 | 0.33 |
| 19 | Compound 2 | 1.2 | 100 | 0.06 | 98 | 0.08 |
| 20 | Compound 2 | 5.2 | 105 | 0.06 | 105 | 0.08 |
| 21 | Compound 3 | 6.6 | 100 | 0.06 | 103 | 0.08 |
| 22 | Compound 4 | 7.0 | 100 | 0.06 | 100 | 0.08 |
| 23 | Compound 6 | 7.9 | 100 | 0.06 | 97 | 0.08 |
| 24 | Compound 5 | 7.7 | 100 | 0.06 | 100 | 0.08 |
| 25 | Compound 8 | 8.4 | 100 | 0.06 | 105 | 0.08 |
| 26 | Compound 11 | 7.3 | 103 | 0.06 | 107 | 0.08 |
| 27 | Compound 14 | 24.8 | 100 | 0.06 | 100 | 0.08 |

Dimedone (Comparison compound)

[Structure of dimedone: 5,5-dimethyl-1,3-cyclohexanedione]

U.S. Pat. No. 3,447,926

It can be apparent from the results shown in Table 2 that the comparison compound can prevent the fading of latent image only when it is added to a silver halide emulsion in an amount of 120 mg/mol AgX or more (preferably 485 mg or more) as described in U.S. Pat. No. 3,447,926 and some decrease in the sensitivity is also accomplished by the use of the compound in such an effective range. On the contrary, the compounds according to the present invention sufficiently prevent the fading of latent image by use even in an extremely small amount, and do not cause any decrease in sensitivity (rather, some increase in the sensitivity occurs in certain cases).

EXAMPLE 3

To a silver iodobromide emulsion containing 4 mol% of silver iodide (average particle size of the silver halide being about 0.4 microns) sensitized with gold and sulfur was added the compound according to the present invention or the comparison compound as shown in Table 3. Further, the various additives described below were added to the emulsion and the resulting mixture was coated and dried to prepare Samples 31 to 38.

These samples were exposed through a yellow filter and an optical wedge for sensitometry, and divided into two portions. One portion was subjected to the color development processing described below just after the light-exposure, and the other portion was stored in a dark place under conditions of a temperature of 35° C. and a relative humidity of 70% for 4 weeks and then subjected to the same processing.

In Table 3, the sensitivity of Sample 31 when developed just after the light-exposure is taken as 100 and the other sensitivities are shown relatively.

Additives

Coupler: 1-(2,4,6-Trichlorophenyl)-3-[3-(2,4-di-tert-amylphenoxyacetamido)benzamido]-5-pyrazolone Spectral Sensitizer: Bis-{2-[1-ethyl-3-(3-sulfopropyl)-5,6-dichlorobenzimidazole]}trimethinecyanine sodium salt Stabilizer: 4-Hydroxy-6-methyl-1,3,3a,7-tetraazaindene Hardening Agent: 2,4-Dichloro-6-hydroxy-1,3,5-triazine sodium salt Auxiliary Coating Agents: Sodium p-dodecylbenzenesulfonate Sodium p-nonylphenoxypoly(ethyleneoxy)propanesulfonate

| Color Development Processing | | |
|---|---|---|
| Processing Step | Temperature (°C.) | Time |
| 1. Color development | 33 | 3 min 30 sec |
| 2. Bleach-fixing | 33 | 1 min 30 sec |
| 3. Washing with water | 25 to 30 | 2 min 30 sec |

The processing solutions used had the following compositions:

| Color Development Solution | | |
|---|---|---|
| Benzyl Alcohol | 15 | ml |
| Diethylene Glycol | 8 | ml |
| Ethylenediaminetetraacetic Acid | 5 | g |
| Sodium Sulfite | 2 | g |
| Anhydrous Potassium Carbonate | 30 | g |
| Hydroxylamine Sulfate | 3 | g |
| Potassium Bromide | 0.6 | g |
| 4-Amino-N-ethyl-N-(β-methanesulfonamidoethyl)-m-toluidine Sesquisulfate Monohydrate | 5 | g |
| Water to make | 1 | liter |
| pH 10.2 | | |

| Bleach-Fixing Solution | | |
|---|---|---|
| Ethylenediaminetetraacetic Acid | 2 | g |
| Ferric Salt of Ethylenediaminetetraacetate | 40 | g |
| Sodium Sulfite | 5 | g |
| Ammonium Thiosulfate | 70 | g |
| Water to make | 1 | liter |

TABLE 3

| Sample No. | Compound | Amount Added (mg/mol AgX) | Developed Just after Light-exposure | | Developed after Standing at 50° C. and 75% RH for 1 Week after Light-exposure | |
|---|---|---|---|---|---|---|
| | | | Relative Sensitivity | Fog | Relative Sensitivity | Fog |
| 31 | Control | — | 100 | 0.16 | 68 | 0.18 |
| 32 | Compound 2 | 3.5 | 100 | 0.16 | 95 | 0.18 |
| 33 | Compound 2 | 6.0 | 102 | 0.16 | 102 | 0.18 |
| 34 | Compound 2 | 9.5 | 105 | 0.17 | 108 | 0.18 |
| 35 | Compound 14 | 15.5 | 100 | 0.16 | 100 | 0.18 |
| 36 | Dimedone (Comparison) | 120 | 97 | 0.19 | 88 | 0.25 |
| 37 | Dimedone (Comparison) | 480 | 93 | 0.28 | 95 | 0.46 |

TABLE 3-continued

| Sample No. | Compound | Amount Added (mg/mol AgX) | Developed Just after Light-exposure | | Developed after Standing at 50° C. and 75% RH for 1 Week after Light-exposure | |
|---|---|---|---|---|---|---|
| | | | Relative Sensitivity | Fog | Relative Sensitivity | Fog |
| 38 | Dimedone + 4-Phenyl urazole | 480 7000 | 91 | 0.17 | 93 | 0.19 |

It is apparent from the results shown in Table 3 that the comparison compound dimedone (and even dimedone plus 4-phenyl urazole) can prevent the fading of latent image only when the dimedone is added to the silver halide emulsion in a large amount, and causes the decrease in sensitivity in such a range. On the contrary, the compounds according to the present invention sufficiently prevent the fading of latent image by the use in extremely small amount, and do not cause the decrease in sensitivity (rather, some increase in the sensitivity occurs in certain cases) in the color processing.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive element comprising a support having thereon at least one silver halide emulsion layer, wherein at least one compound represented by formula (I) is incorporated in the silver halide emulsion layer or in another hydrophilic colloid layer:

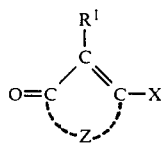

(I)

wherein X represents a hydroxy group or a group represented by

wherein $R^2$ and $R^3$ each repesents hydrogen, an alkyl group, or an aryl group; $R^1$ represents a sulfur-containing saturated heterocyclic group or a group represented by -A-S-B, wherein A represents an alkylene group and B represents hydrogen, an alkyl group, or an aryl group; and Z represents an atomic group forming a 5-membered or 6-membered unsubstituted or substituted carbocyclic ring.

2. A silver halide photographic light-sensitive elements as in claim 1, wherein the alkyl group represented by $R^2$ or $R^3$ is an alkyl group having from 1 to 5 carbon atoms.

3. A silver halide photographic light-sensitive element as in claim 1, wherein the aryl group represented by $R^2$ or $R^3$ is a phenyl group.

4. A silver halide photographic light-sensitive element as in claim 1, wherein one of $R^2$ and $R^3$ is hydrogen.

5. A silver halide photographic light-sensitive element as in claim 1, wherein the sulfur-containing saturated heterocyclic group represented by $R^1$ is a 5-membered or 6-membered heterocyclic group containing at least one sulfur atom as a ring constituting member and connecting to the carbocyclic ring in formula (I) through a carbon atom adjacent to the sulfur atom.

6. A silver halide photographic light-sensitive element as in claim 1, wherein the sulfur-containing saturated heterocyclic group represented by $R^1$ is a 2-tetrahydrothienyl group or a tetrahydrothiopyranyl group.

7. A silver halide photographic light-sensitive element as in claim 1, wherein the sulfur-containing saturated heterocyclic group represented by $R^1$ is substituted with one or more substituents selected from a methyl group, an ethyl group, a methoxy group, and an acetamido group.

8. A silver halide photographic light-sensitive element as in claim 1, wherein A in the group represented by -A-S-B is a methylene group.

9. A silver halide photographic light-sensitive element as in claim 1, wherein the alkyl group represented by B is an alkyl group having from 1 to 12 carbon atoms.

10. A silver halide photographic light-sensitive element as in claim 1, wherein the aryl group represented by B is a phenyl group.

11. A silver halide photographic light-sensitive element as in claim 1, wherein the group represented by -A-S-B is a mercaptoethyl group, an ethylthiomethyl group, a dodecylthiomethyl group, or a phenylthiomethyl group.

12. A silver halide photographic light-sensitive element as in claim 1, wherein $R^1$ is a sulfur-containing saturated heterocyclic group.

13. A silver halide photographic light-sensitive element as in claim 1, wherein the 5-membered or 6-membered carbocyclic ring formed with Z is a cyclopentene ring or a cyclohexene ring.

14. A silver halide photographic light-sensitive element as in claim 1, wherein the 5-membered or 6-membered carbocyclic ring formed by Z is substituted with one or more substituents selected from an alkyl group and an aryl group.

15. A silver halide photographic light-sensitive element as in claim 14, wherein the alkyl group substituted on the 5-membered or 6-membered carbocyclic ring is an alkyl group having from 1 to 5 carbon atoms.

16. A silver halide photographic light-sensitive element as in claim 14, wherein the aryl group substituted on the 5-membered or 6-membered carbocyclic ring is a phenyl group which can be substituted with one or more substituents selected from an alkyl group, an alkoxy group, and a halogen atom.

17. A silver halide photographic light-sensitive element as in claim 15, wherein the alkyl group is a methyl group or an ethyl group.

18. A silver halide photographic light-sensitive element as in claim 16, wherein the aryl group is a phenyl group, a p-tolyl group, a p-iso-propylphenyl group, a p-methoxyphenyl group, a 3,4-dimethoxyphenyl group, a 3,4,5-trimethoxyphenyl group, or a 3,4-dichlorophenyl group.

19. A silver halide photographic light-sensitive element as in claim 1, wherein the compound represented by formula (I) is incorporated in the element in the form of a salt thereof.

20. A silver halide photographic light-sensitive element as in claim 19, wherein the salt is a hydrochloride, a sulfate, or an acetate.

21. A silver halide photographic light-sensitive element as in claim 1, 5, 6, 7, 8, 9, 10, 11, 12, 19, or 20, wherein the compound represented by formula (I) is incorporated into a silver halide emulsion layer.

22. A silver halide photographic light-sensitive element as in claim 1, 5, 6, 7, 8, 9, 10, 11, 12, 19, or 20, wherein the compound represented by formula (I) is incorporated into a light-insensitive layer.

23. A silver halide photographic light-sensitive element as in claim 21, wherein the amount of the compound represented by formula (I) is from 0.05 mg/mol Ag to 100 mg/mol Ag.

24. A silver halide photographic light-sensitive element as in claim 21, wherein the amount of compound represented by formula (I) is from 0.1 mg/mol Ag to 50 mg/mol Ag.

25. A silver halide photographic light-sensitive element as in claim 1, wherein a silver halide emulsion of the silver halide emulsion layer is chemically sensitized.

26. A silver halide photographic light-sensitive element as in claim 1, wherein a silver halide emulsion of the silver halide emulsion layer is spectrally sensitized.

27. A silver halide photographic light-sensitive element as in claim 1, wherein the silver halide emulsion layer further contains a color image forming coupler.

* * * * *